(12) United States Patent
Kuo et al.

(10) Patent No.: US 11,749,398 B2
(45) Date of Patent: Sep. 5, 2023

(54) MEDICAL IMAGE RECOGNITION SYSTEM AND MEDICAL IMAGE RECOGNITION METHOD

(71) Applicant: Quanta Computer Inc., Taoyuan (TW)

(72) Inventors: Kuei-Hong Kuo, Taoyuan (TW); Hao Wang, Taoyuan (TW); Chung-Yi Yang, Taoyuan (TW); Kuan-Chieh Huang, Taoyuan (TW); Bo-Yu Lin, Taoyuan (TW); Yi-Ting Peng, Taoyuan (TW); Ching-Chung Kao, Taoyuan (TW)

(73) Assignee: QUANTA COMPUTER INC., Taoyuan (TW)

( * ) Notice: Subject to any disclaimer, the term of this patent is extended or adjusted under 35 U.S.C. 154(b) by 547 days.

(21) Appl. No.: 16/933,163

(22) Filed: Jul. 20, 2020

(65) Prior Publication Data

US 2021/0202089 A1 Jul. 1, 2021

(30) Foreign Application Priority Data

Dec. 27, 2019 (TW) .................................. 108147976

(51) Int. Cl.
*G06K 9/00* (2022.01)
*G16H 30/20* (2018.01)
(Continued)

(52) U.S. Cl.
CPC ............. *G16H 30/20* (2018.01); *G06F 18/24* (2023.01); *G06N 3/02* (2013.01); *G06V 10/764* (2022.01); *G06V 10/809* (2022.01); *G06V 10/82* (2022.01); *G16H 10/60* (2018.01); *G16H 15/00* (2018.01); *G16H 50/20* (2018.01); *G16H 50/30* (2018.01)

(58) Field of Classification Search
None
See application file for complete search history.

(56) References Cited

U.S. PATENT DOCUMENTS 11,195,600 B2 * 12/2021 Rajan ..................... G16H 15/00
2019/0114766 A1 * 4/2019 Song ....................... G06T 7/0012
(Continued)

FOREIGN PATENT DOCUMENTS

| CN | 108986908 A | 12/2018 |
| CN | 109378043 A | 2/2019 |
| CN | 109545302 A | 3/2019 |

OTHER PUBLICATIONS

Taiwan Office Action, dated Nov. 3, 2020, in application No. 108147976.
(Continued)

*Primary Examiner* — Avinash Yentrapati
(74) *Attorney, Agent, or Firm* — McClure, Qualey & Rodack, LLP

(57) ABSTRACT

The medical image recognition method includes the following steps: transmitting an accession number to a recognition module through a prediction unit; receiving an accession number and a human body image by a recognition model, and importing the human body image into a set of neural network models respectively; wherein each of the neural network models outputs at least one recognition result; the recognition module returns the recognition results to the prediction unit, and then the recognition results are stored in database.

6 Claims, 7 Drawing Sheets

(51) Int. Cl.
    *G16H 50/20*         (2018.01)
    *G16H 50/30*         (2018.01)
    *G16H 10/60*         (2018.01)
    *G16H 15/00*         (2018.01)
    *G06N 3/02*          (2006.01)
    *G06F 18/24*         (2023.01)
    *G06V 10/764*       (2022.01)
    *G06V 10/80*         (2022.01)
    *G06V 10/82*         (2022.01)

(56)             References Cited

U.S. PATENT DOCUMENTS

| | | | |
|---|---|---|---|
| 2019/0326007 A1* | 10/2019 | Sharma | G16H 30/40 |
| 2020/0104994 A1* | 4/2020 | Sharma | G06T 11/003 |
| 2020/0211692 A1* | 7/2020 | Kalafut | G06N 20/00 |
| 2021/0327563 A1* | 10/2021 | He | G06V 10/235 |
| 2022/0122730 A1* | 4/2022 | Hayashi | G06V 40/13 |

OTHER PUBLICATIONS

Search report accompanying Taiwan Office Action, dated Nov. 3, 2020, in application No. 108147976.
Chinese language office action dated Mar. 10, 2021, issued in application No. TW 108147976.

\* cited by examiner

| disease diagnosis 310 | in-body medical device detection 320 | auxiliary determination 330 |
|---|---|---|
| Normal/Abnormal | ETT | Heart detection |
| Pneumothorax | CVC | Lung detection |
| Pleural effusion | Stent | Posture recognition |
| Cardiomegaly | Pacemaker | Gender recognition |
| Lung mass (nodule) | Pigtail | Lung age estimation |
| Pneumonia | Port A | Mediastinum |
| Acute Heart Failure | NG | |
| Aorta calcification | Chest tube | |
| Sternotomy | | |
| Pneumo-peritoneum | | |
| Apical Pleural Thickening | | |
| Clavicle fracture | | |

FIG. 3

MEDICAL IMAGE RECOGNITION SYSTEM AND MEDICAL IMAGE RECOGNITION METHOD

CROSS REFERENCE TO RELATED APPLICATIONS

This Application claims priority of Taiwan Patent Application No. 108147976, filed on Dec. 27, 2019, the entirety of which is incorporated by reference herein.

BACKGROUND OF THE INVENTION

Field of the Invention

The present disclosure relates to a medical recognition system and, in particular, to a medical image recognition system and a medical image recognition method.

Description of the Related Art

A certain proportion of hospitals find that, in general, they are unable to immediately complete a report on the interpretation of a chest X-ray image, due to insufficient comprehensive medical manpower and resources.

Lesions are faint or easy to miss, and reports cannot be completed immediately (or human resources are insufficient for completing the report), which results in medical disputes, and medical disputes are increasing day by day.

Therefore, how to improve the efficiency of completing a report and how to detect abnormal cases using limited manpower have become urgent performance targets in this field.

BRIEF SUMMARY OF THE INVENTION

In accordance with one feature of the present invention, the present disclosure provides a medical image recognition system. The medical image recognition system includes a first unit and a recognition module. The first unit transmits an accession number. The recognition module receives the accession number and a body image, and input the body image into a plurality of neural network models. Each of the neural network models outputs at least one recognition result, and the recognition module returns the recognition results to the first unit. In addition, the first unit stores the recognition results in a database.

In one embodiment, the database transmits medical-record data corresponding to the accession number to the first unit, the first unit combines the accession number, the medical-record data and the recognition results into a raw result, and returns the raw result to the database.

In one embodiment, the medical image recognition system further includes an integration unit. The integration unit receives the accession number from the first unit, reads the raw result from the database according to the accession number, modifies the raw result to recognition results according to a plurality of reporting rules, generates a recognition report according to the adjusted recognition results, and stores the recognition report in the database. In addition, data of the recognition results have dependencies on each other, when the data of the recognition results are in conflict or mutually exclusive, the integration unit modifies at least one of the recognition results in the raw result according to the reporting rules.

In one embodiment, the medical image recognition system further includes a digital imaging and communications in medicine (DICOM) reader. The digital imaging and communications in medicine (DICOM) reader receives the accession number from a web server and a DICOM image file from DICOM image storage, and converts the DICOM image file into a portable network graphics (PNG) image file in a PNG image format, and then stores the PNG image file into a PNG image storage device; wherein the DICOM image file conforms to the DICOM format, and the PNG image file includes the body image.

In one embodiment, an automated reporting system reads the recognition report corresponding to the accession number from the database and displays the recognition report on a display through a user interface. In addition, the automated reporting system receives the modified information through the user interface and writes the modified information into the database according to the accession number.

In accordance with one feature of the present invention, the present disclosure provides a medical image recognition method. The medical image recognition method includes the following steps: a first unit transmits an accession number; a recognition module receives the accession number and a body image and inputs the body image into a plurality of neural network models; each of the neural network models outputs at least one recognition result; the recognition module returns the recognition results to the first unit; and the first unit stores the recognition results in a database.

In one embodiment, the database transmits medical-record data corresponding to the accession number to the first unit, the first unit combines the accession number, the medical-record data and the recognition results into a raw result, and returns the raw result to the database.

In one embodiment, the medical image recognition method further includes the following steps: using an integration unit to receive the accession number from the first unit, reading the raw result from the database according to the accession number, modifying the raw result to recognition results according to a plurality of reporting rules, generating a recognition report according to the modified recognition results, and storing the recognition report in the database. In addition, the recognition results have data dependencies on each other. When the data of the recognition results are in conflict or mutually exclusive, the integration unit modifies at least one of the recognition results according to the reporting rules.

In one embodiment, the medical image recognition method further includes the following steps: receiving the accession number from a web server and a DICOM image from DICOM image storage by a digital imaging and communications in medicine (DICOM) reader, and converting the DICOM image into a portable network graphics (PNG) image in a PNG file format, and then storing the PNG image into a PNG image storage device; wherein the DICOM image conforms to the DICOM file format, and the PNG image file comprises the body image.

In one embodiment, the medical image recognition method further includes the following steps: reading the recognition report corresponding to the accession number from the database using an automated reporting system and displaying the recognition report on a display through a user interface; and, the automated reporting system receives a modified information through the user interface and writes the modified information into the database according to the accession number.

In summary, the medical image recognition system and the medical image recognition method in the present invention can assist medical personnel in medical diagnosis, improve diagnosis efficiency, and analyze body images by applying a neural network model to achieve the effect of obtaining more accurate recognition results.

BRIEF DESCRIPTION OF THE DRAWINGS

In order to describe the manner in which the above-recited and other advantages and features of the disclosure can be obtained, a more particular description of the principles briefly described above will be rendered by reference to specific examples thereof which are illustrated in the appended drawings. Understanding that these drawings depict only example aspects of the disclosure and are not therefore to be considered to be limiting of its scope, the principles herein are described and explained with additional specificity and detail through the use of the accompanying drawings in which:

FIG. 3 is a schematic diagram of recognition functions of a recognition module in accordance with one embodiment of the present disclosure.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The present invention will be described with respect to particular embodiments and with reference to certain drawings, but the invention is not limited thereto and is only limited by the claims. It will be further understood that the terms "comprises," "comprising," "comprises" and/or "including," when used herein, specify the presence of stated features, integers, steps, operations, elements, and/or components, but do not preclude the presence or addition of one or more other features, integers, steps, operations, elements, components, and/or groups thereof.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Figure 1:
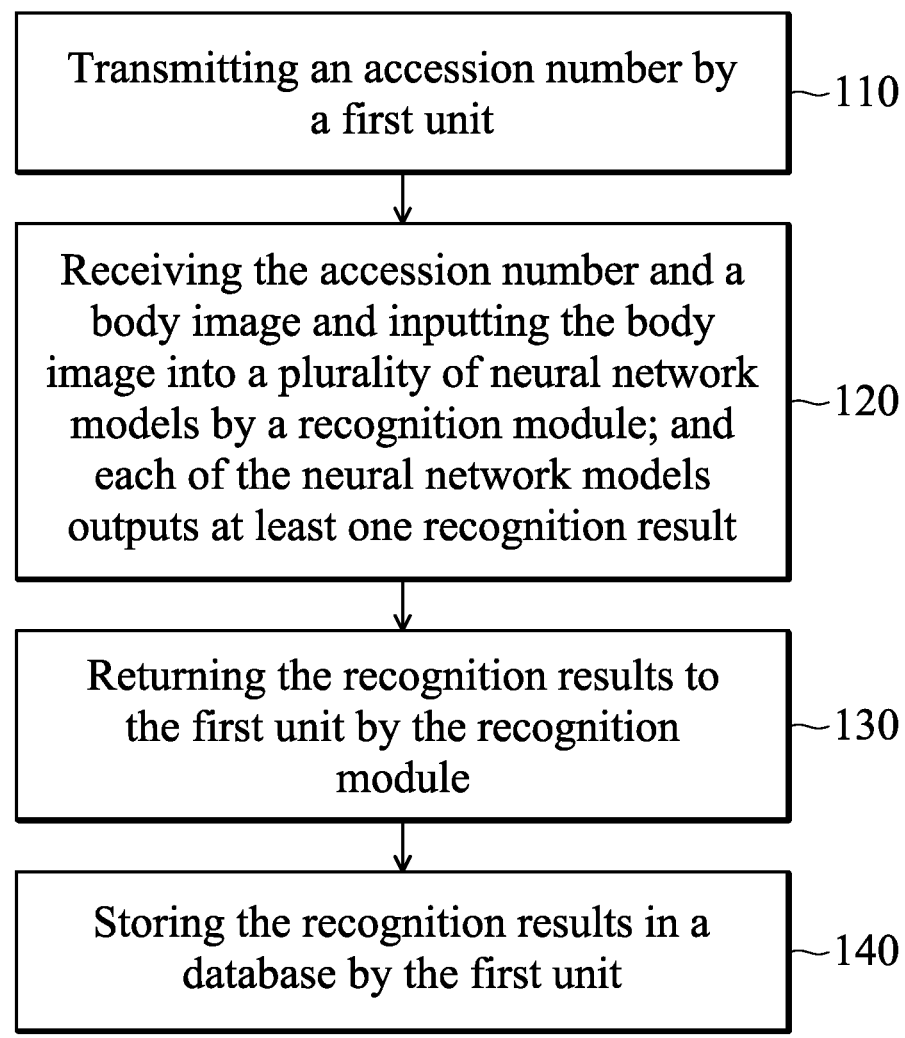
FIG. 1 is a flowchart of a medical image recognition method in accordance with one embodiment of the present disclosure.
Figure 2:
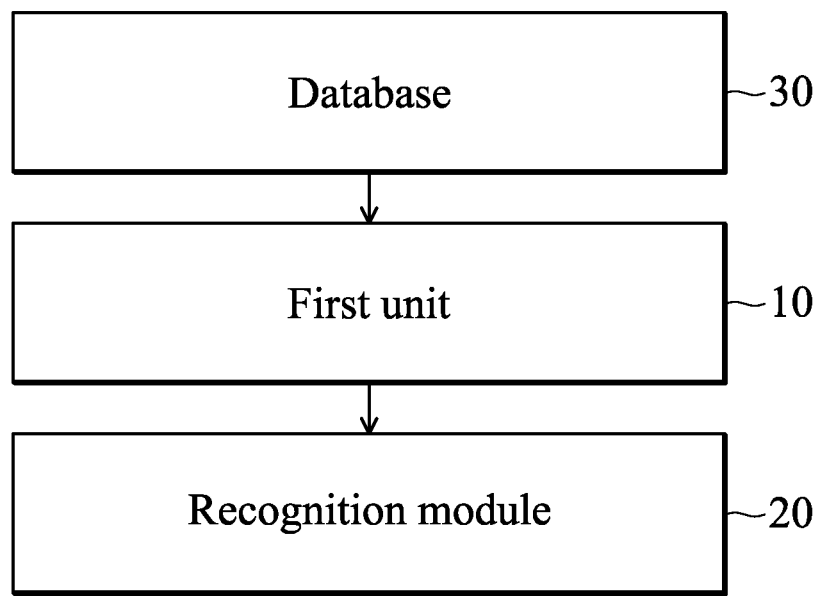
FIG. 2 is a block diagram of a medical image recognition system in accordance with one embodiment of the present disclosure.

Please refer to FIGS. 1-3, FIG. 1 is a flowchart of a medical image recognition method 100 in accordance with one embodiment of the present disclosure. FIG. 2 is a block diagram of a medical image recognition system 200 in accordance with one embodiment of the present disclosure. FIG. 3 is a schematic diagram of recognition functions of a recognition module 20 in accordance with one embodiment of the present disclosure.

In step 110, a first unit 10 transmits an accession number.

In one embodiment, the first unit 10 can be any electronic device having a calculation function. In one embodiment, the first unit 10 can be implemented using a micro controller, such as a microcontroller, a microprocessor, a digital signal processor, a field programmable gate array, an application specific integrated circuit (ASIC), or a logic circuit.

In one embodiment, the accession number can be the data sheet number of the patient during the physical examination.

In step 120, a recognition module 20 receives the accession number and a body image and inputs the body image into a plurality of neural network models; and each of the neural network models outputs at least one recognition result.

In one embodiment, the body image is, for example, a chest X-ray image.

In one embodiment, the recognition module 20 is used to execute algorithms of neural network models. In one embodiment, the recognition module 20 can be any electronic device having a calculation function. In one embodiment, the recognition module 20 can be implemented using a micro controller, such as a microcontroller, a microprocessor, a digital signal processor, a field programmable gate array, an application specific integrated circuit (ASIC), or a logic circuit.

Referring to FIG. 3, the recognition module 20 can recognize the 26 detection items in FIG. 3 through multiple neural network models. In one embodiment, the multiple neural network models can be implemented by using different algorithms. For example, the multiple neural network models can be classified into classification type, object detection type, regression type, and image segmentation type.

The classification type is known algorithm, such as InceptionResNetV2, ResNet, and/or VGG, which can output image analyze results. For example, in the disease diagnosis 310 in FIG. 3, for the pneumothorax item, a neural network model can detect pneumothorax and display the diseased area with a heat map.

The object detection type is known algorithm, such as SSD, YOLOV3, RetinaNet, etc. For example, the in-body medical device detection 320 in FIG. 3 contains items that are classified to the detection-type neural network model. The detection-type neural network model can output a partial area selection box or substitute the output value into a medical formula. For example, the items of the in-body medical device detection 320 in FIG. 3 can detect a stent and a central venous catheter in the X-ray image. In another example, the method for determining cardiomegaly in FIG. 3 is to frame the positions of the heart and lungs by using a object detection type neural network model, and then divide the heart-framed area by the lung-framed area and use the calculated results to determine cardiomegaly.

The regression type is a special case of the classification type. Basically, the algorithm used by the regression type is the same as the classification type, which can output a value. For example, in the items of the auxiliary determination 330 in FIG. 3, the regression-type neural network model estimates that the lung age is 23 years old.

The image segmentation type is a known algorithm, such as Fully Convolutional Networks (FCNs), DeepLab, Mask R-CNN, etc. The image segmentation type displays the results in pixels. For example, in the disease diagnosis 310 in FIG. 3, for a lung mass item, an image segmentation-type neural network model can detect whether there is a lung mass in this medical image, and mark the location of the symptom or its contour in pixels.

In one embodiment, FIG. 3 includes a total of 26 detection items. The X-ray image is input into the 26 neural network model to produce the recognition results corresponding to these 26 detection items. However, it should be understood by those having ordinary knowledge in the art that the present invention is not limited to the number of detection items, and here is one example for explanation.

In step 130, the recognition module 20 returns the recognition results to the first unit 10.

In step 140, the first unit 10 stores the recognition results in a database 30.

In one embodiment, the database 30 can be stored in a storage device. The storage device can be implemented as a read-only memory, a flash memory, a floppy disk, a hard disk, a compact disk, a flash drive, a tape, a network accessible database, or as a storage medium that can be easily considered by those skilled in the art to have the same function.

Figure 4:
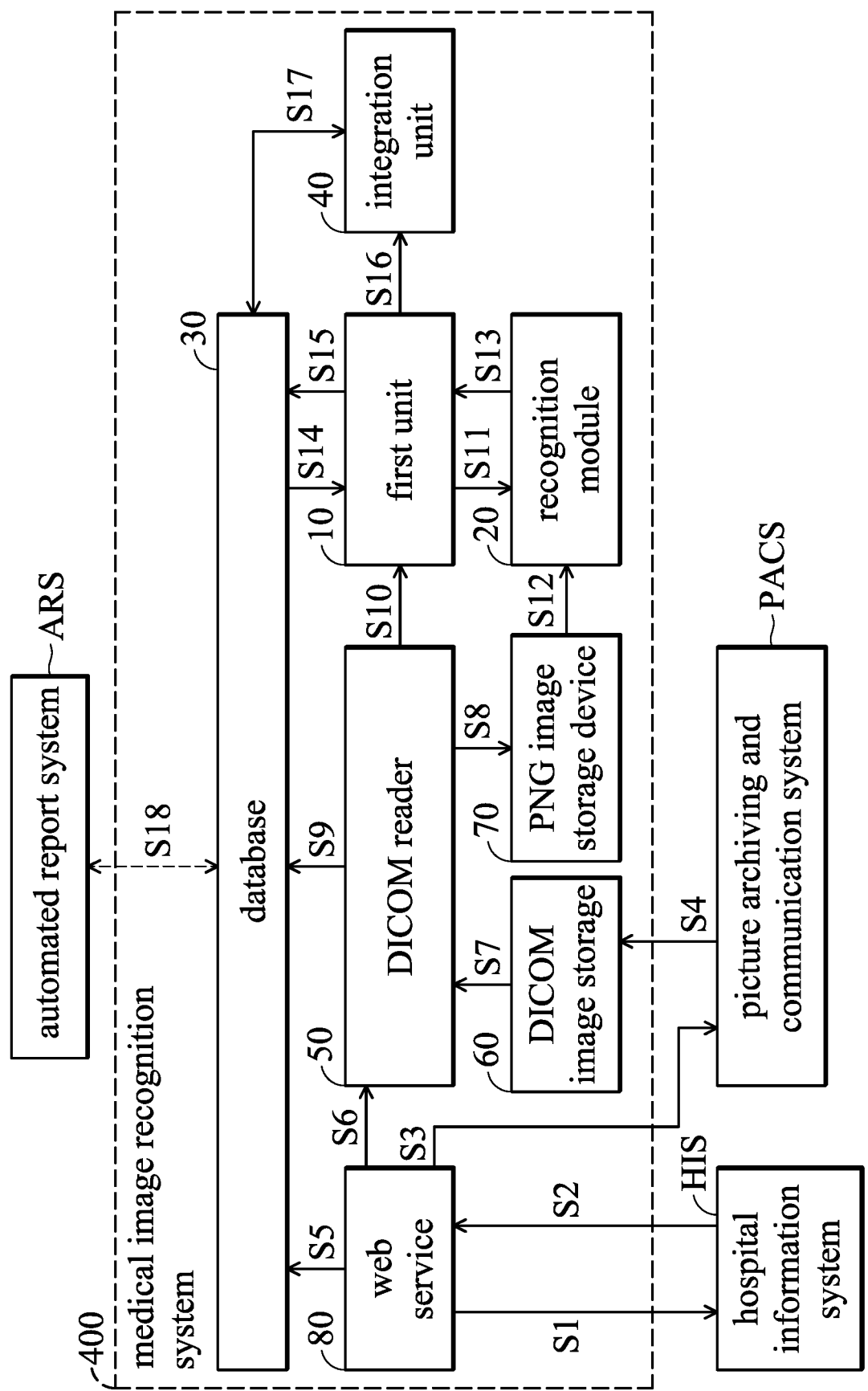
FIG. 4 is a block diagram of a medical image recognition system in accordance with one embodiment of the present disclosure.
Figure 5:
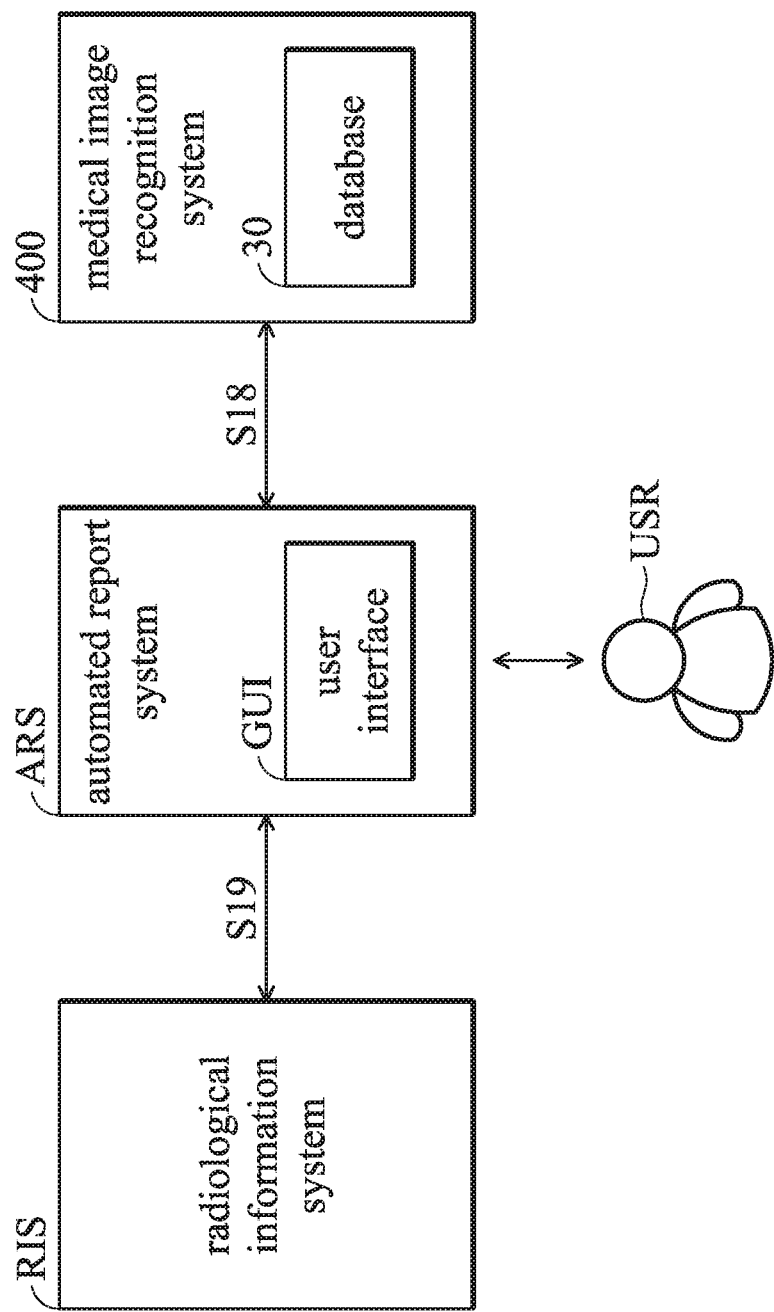
FIG. 5 is a schematic diagram of an automatied report generation method in accordance with one embodiment of the present disclosure.
Figure 6:
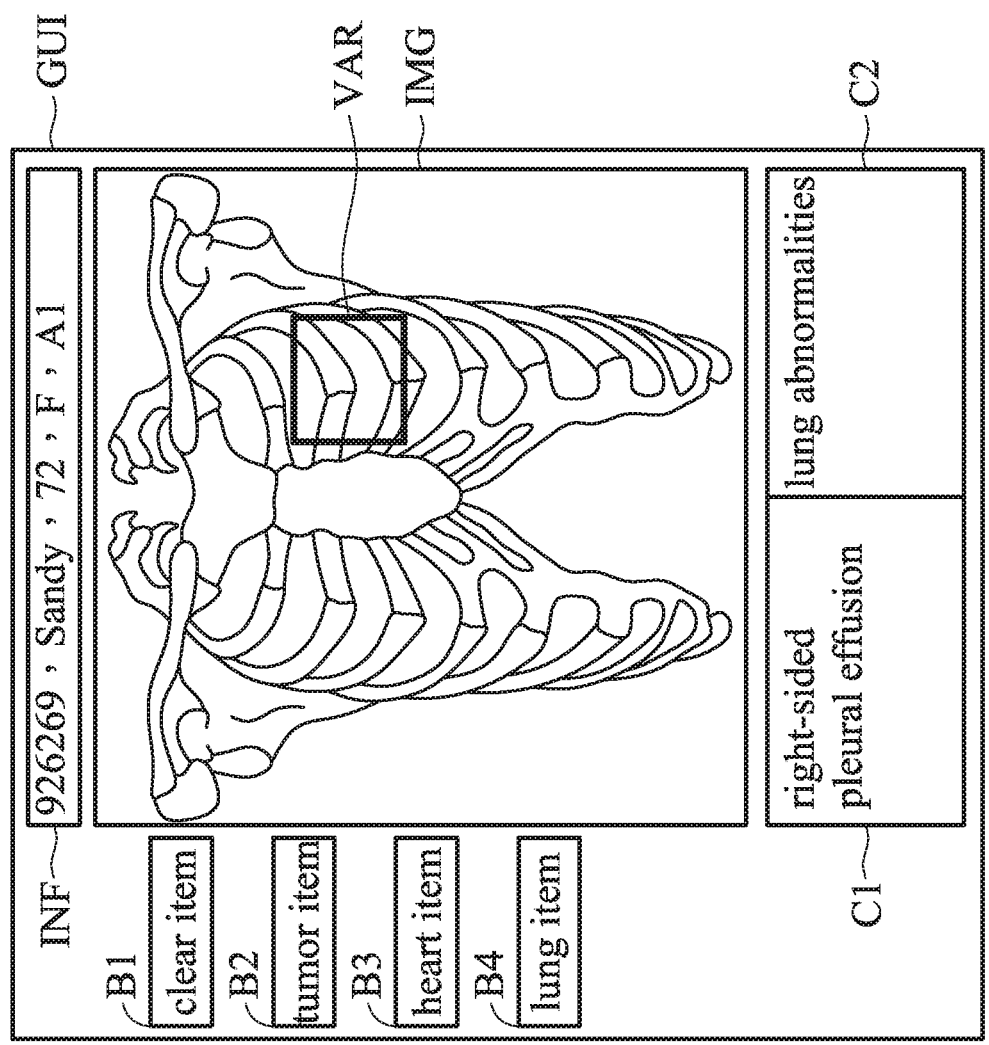
FIG. 6 is a schematic diagram of a user interface in accordance with one embodiment of the present disclosure.
Figure 7:
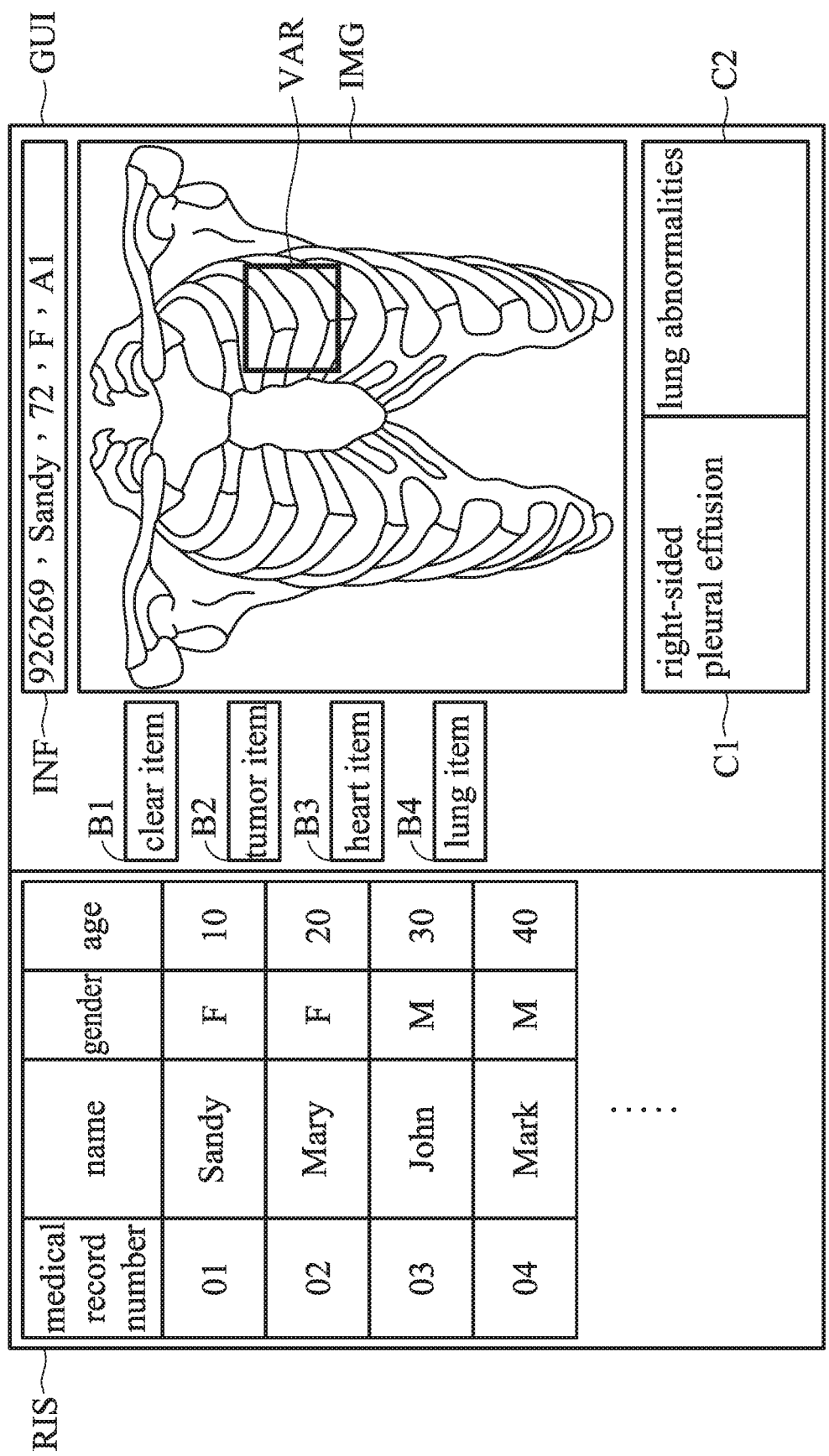
FIG. 7 is a schematic diagram of an operation interface in accordance with one embodiment of the present disclosure.

Please refer to FIGS. 4-7, FIG. 4 is a block diagram of a medical image recognition system 400 in accordance with one embodiment of the present disclosure. FIG. 5 is a schematic diagram of an automatic report generation method in accordance with one embodiment of the present disclosure. FIG. 6 is a schematic diagram of a user interface GUI in accordance with one embodiment of the present disclosure. FIG. 7 is a schematic diagram of an operation interface in accordance with one embodiment of the present disclosure.

In one embodiment, as shown in FIG. 4, the medical image recognition system 400 can establish a communication link between the hospital information system HIS, the picture archiving and communication system PACS, and/or the automated report system ARS in a wired/wireless manner. In general, the hospital information system HIS, the picture archiving and communication system PACS are the systems located inside the hospital.

In one embodiment, the hospital information system HIS refers to all information tools, information systems, etc., used by a hospital for diagnosis, treatment, management, logistics and other services. In other words, the hospital information system HIS is a system for storing patient data. For example, the stored information is a patient identification code and/or medical-record data.

In one embodiment, the picture archiving and communication system PACS is used to acquire image data from medical image inspection equipment, and then process, store, retrieve, display, and intelligently identify medical images, and so on.

In one embodiment, as shown in FIG. 4, the medical image recognition system 400 includes a database 30, a first unit 10 and a recognition module 20. The database 30, the first unit 10, and the recognition module 20 shown in FIG. 4 are the same as the database 30, the first unit 10, and the recognition module 20 in FIG. 2. It will not further describe herein. In one embodiment, FIG. 4 further includes an integration unit 40, a digital imaging and communications in medicine (DICOM) reader 50, DICOM image storage 60, a portable network graphics (PNG) image storage device 70, and a web service 80.

In an embodiment, the integration unit 40 and the DICOM reader 50 can be separately implemented by using an integrated circuit, such as a microcontroller, a microprocessor, a digital signal processor, an application specific integrated circuit, or a logic circuit.

In one embodiment, the DICOM image storage 60 and the PNG image storage device 70 may be implemented by a storage device, respectively.

In one embodiment, the web server 80 can be a server or an electronic device with transmission, storage, and calculation functions.

In step S1, the web server 80 sends a time interval to the hospital information system HIS.

In one embodiment, the web server 80 sends a time interval (for example, 2 hours) to the hospital information system HIS, which represents the web server 80 having requested information from the hospital information system HIS on all patients who were examined during this time interval. For example, the patient's information maybe medical-record data. The medical-record data includes examination information, medical record number, ID card number, name, gender, date of examination, whether it is a new diagnosis, etc.

In step S2, the hospital information system HIS returns the data of all patients examined during this time interval to the web server 80.

For example, when 50 patients were examined at the hospital during the two hours, the hospital information system HIS returns the data of the 50 patients to the network server 80.

In step S3, the web server 80 sends an image file request corresponding to a user to the picture archiving and communication system PACS. The image file request is used to drive the picture archiving and communication system PACS to retrieve a medical image file corresponding to the user. For example, the medical image file is a computer tomography file and/or an X-ray image.

In step S4, the picture archiving and communication system PACS sends an X-ray image file corresponding to the user to the DICOM image storage 60. In one embodiment, the picture archiving and communication system PACS can also send computer tomography files or other medical image files to the DICOM image storage 60 for subsequent processing. However, for convenience of description, the X-ray image is taken as an example for illustration.

In step S5, the web server 80 sends the medical-record data and the accession number corresponding to the medical-record data to the database 30.

For example, the web server 80 generates an accession number according to the medical-record data. The accession number is used to represent the medical-record data of the patient, and the medical-record data is recorded during the examination.

In step S6, the web server 80 sends the accession number to the DICOM reader 50.

In step S7, the DICOM image storage 60 transmits the X-ray image file to the DICOM reader 50.

In one embodiment, the DICOM reader 50 pre-processes the X-ray image. For example, X-ray images are in the DICOM image format. The DICOM reader 50 converts the X-ray image file into a PNG image file in the PNG image format.

In step S8, the DICOM reader 50 converts the X-ray image into a PNG image in a PNG image format, and then stores the PNG image into a PNG image storage device 70.

In one embodiment, the PNG image includes a body image. Or, the PNG image itself can be a body image.

In step S9, the DICOM reader 50 stores the X-ray image conforming to the DICOM image format in the database 30.

In step S10, the DICOM reader 50 transmits the accession number to the first unit 10.

In step S11, the first unit 10 transmits the accession number to the recognition module 20.

In step S12, the PNG image storage device 70 transmits the PNG image to the recognition module 20.

In one embodiment, the recognition module 20 extracts the body image part in the PNG image, and inputs the body image into multiple neural network models, respectively. Each of these neural network models outputs at least one recognition result. Since the processing performed by the recognition module 20 in this step is the same as step 120 in FIG. 1, it will not be repeated here.

In step S13, the recognition module 20 returns these recognition results to the first unit 10.

In step S14, the database 30 transmits the medical-record data corresponding to the accession number to the first unit 10.

In step S15, the first unit 10 transmits a raw result to the database 30.

In one embodiment, the database 30 sends the medical-record data corresponding to the accession number to the first unit 10. The first unit 10 combines the accession number, the medical-record data, and these recognition results into a raw result. The first unit 10 then transmits the raw result to the database 30.

In one embodiment, the first unit 10 transmits the medical-record data and the accession number corresponding to the medical-record data to the database 30.

In step S16, the first unit 10 transmits the accession number to the integration unit 40.

In step S17, the integration unit 40 reads the raw result from the database 30 according to the accession number, and modifies the raw result to recognition results according to a plurality of reporting rules, generates a recognition report according to the modified recognition results, and stores the recognition report in the database 30.

In one embodiment, the reporting rules can be some medical rules defined in advance by a doctor. For example, one of the reporting rules is defined as: a person only has 1 heart. Therefore, when the recognition report shows that 3 hearts are detected in a person's body, it means that the recognition report may be misjudged. Since the neural network model can output the confidence probability of the three heart positions, the confidence probability represents the possibility of each of the three heart positions being determined as the heart. Therefore, the integration unit 40 selects one heart position with the highest confidence probability from the three heart positions to modified the recognition report. It can be known that the recognition results of misjudgments can be modified through these reporting rules, and then the modified recognition results are written to the database 30, thereby improving the accuracy of the recognition report.

In one embodiment, the integration unit 40 can firstly review the recognition results of a neural network model for a detection item, and then refer to the recognition results of several neural network models related to the detection item and compare these recognition results with each other (for example, the first recognition result frames 3 cardiac abnormalities by selection boxes, and the second recognition result frames 1 cardiac abnormality by a selection box). Since data of the recognition results have dependencies on each other, when the data of multiple recognition results are in conflict or mutually exclusive, at least one of the recognition results is modified according to the relevant reporting rules (for example, it can be known from the reporting rules that a human has only one heart, so the first recognition result should be modified or deleted).

In one embodiment, the accuracy of the neural network model can be evaluated through a comparison of the differences between the recognition result output from the neural network model trained by a validation dataset and the actual doctor's labeling, for example, the evaluation items of the differences can be: whether there are any symptoms, the offsets of the selection box for marking the disease position, and the differences of output values. In one embodiment, during the training stage, a large number of X-ray images are first collected. The doctors are asked to label the answer for whether the diseases shown on these X-ray images. It is divided into training set, validation set and test data set according to different patients and image proportions. The images of training set and validation set are introduced into different layers of the convolutional network in deep learning for data calculation. The testing set is used to evaluate the generalization ability of the model after training. Taken GoogleNet (one kind of neural network model) as an example, after the process of data feature extraction by convolution, data range scaling to a consistent range by normalization, data down-sampling by pooling, etc., the feature data is then processed by fully-connected to output the final recognition result. In addition, the neural network model is repeatedly tuned by the difference between the recognition result and the actual age value. In other words, these recognition results generated during the training stage of the neural network model can be fed back to the neural network model after calculating the errors, so as to optimize the recognition accuracy of the neural network model.

In one embodiment, as shown in FIG. 5, the automated report system ARS accesses the database 30 in the medical image recognition system 400 (step S18). The automated report system ARS modifies the data in the database 30 according to the reporting rules (that is, the reporting term of each symptom or the correlation of a specific symptom) provided by the doctor (for example, the user USR), and automatically generates a report. When the doctor reviews the report, and the patient's patient identification code and/or medical-record data is selected, the display shows the automatically generated report. In addition, the doctor can modify the report through the user interface GUI. When the doctor presses the confirmation report button, the automated report system ARS will send the automatically generated report or the modified report to the radiological information system RIS (step S19). The radiological information system RIS obtains the report for subsequent applications. The application can perform the business processes of radiological examination, such as appointment, registration, reporting and review.

The medical image recognition system 400 in FIG. 5 is the same as the medical image recognition system 400. In order to make the diagram concise, only the database 30 is drawn in the medical image recognition system 400 in FIG. 5. The person having ordinary knowledge in the art can understand that other components of the medical image recognition system 400 omitted showing in FIG. 5 are the same as the medical image recognition system 400 in FIG. 4.

Referring to FIG. 6, the automated report system ARS reads the recognition report corresponding to the accession number from the database 30, and displays the recognition report on a display through a user interface GUI. The automatic report system ARS receives modified information through the user interface GUI, and writes the modified information into the database 30 according to the accession number.

In one embodiment, as shown in FIG. 6, the user interface GUI includes a patient information field INF, a human body image IMG, a clear item B1, a tumor item B2, a heart item B3, a lung item B4, an information field C1, and/or information field C2. The patient information field INF contains the medical record number "926269", name "Sandy", age "72" (years), gender "F" (female), and/or accession number "A1". Those with ordinary skill in the art should be able to understand the contents of the patient information field INF is not limited here, it can also contain other patient-related information. The human body image IMG is, for example, an X-ray image. The clear item B1 means that the user USR can click this button to clear the edited part of the screen. The tumor item B2 represents the recognition result related to the tumor. The heart item B3 represents the recognition result related to the heart. The lung item B4 represents the recognition results related to the lungs. However, those with ordinary skill in the art should be able to understand that these items are only examples. When implementing the user interface GUI, other items can be presented according to the information required by the user USR.

In the example shown in FIG. 6, when the user USR clicks on the lung item B4, a selection box VAR is displayed on the human body image IMG, which represents the recognition result related to the lungs. It is determined that the position of the selection box VAR is abnormal. Further information about the abnormal is written in information fields C1 and C2. The user USR (for example, a doctor) can quickly understand the possible lung problems of the patient through the user interface GUI. If the user USR thinks that the recognition result of the lung is wrong, the user USR can also modify it in the information field C1 and/or information field C2 of the user interface GUI, click the selection box VAR and then press the clear item B1 to clear the clicked selection box VAR, or directly move the clicked selection box VAR to the appropriate position. Then, the automatic report system ARS receives the modification information through the user interface GUI, and writes the modified information into the database 30 according to the accession number.

Please refer to FIG. 7, the user USR can instruct showing the user interface GUI and the information of hospital's radiological information system RIS on the display together. The radiological information system RIS can list the information of multiple patients (such as medical record number, name, gender (the symbol "F" presents female, the symbol "M" presents male), age). When the user USR clicks on the medical record number "01" on the interface of the radial information system RIS, the user interface GUI presents the body image IMG of the patient "Sandy" and the related recognition report.

In summary, the medical image recognition system and the medical image recognition method in the present invention can assist medical personnel in medical diagnosis, improve diagnosis efficiency, and analyze body images by applying a neural network model to achieve the effect of obtaining more accurate recognition results.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such a feature may be combined with one or more other features of the other implementations as may be desired and advantageous for any given or particular application.

What is claimed is:

1. A medical image recognition system, comprising a plurality of integrated circuits configured to implement:
   an integration unit;
   a first unit, wherein the first unit transmits an accession number; and
   a recognition module, wherein the recognition module receives the accession number and a body image, and wherein the recognition module inputs the body image into a plurality of neural network models; wherein each of the neural network models outputs at least one recognition result, and the recognition module returns the recognition results to the first unit;
   wherein the first unit stores the recognition results in a database;
   wherein the database transmits medical-record data corresponding to the accession number to the first unit, the first unit combines the accession number, the medical-record data and the recognition results into a raw result, and returns the raw result to the database; the integration unit receives the accession number from the first unit, reads the raw result from the database according to the accession number, modifies the raw result to recognition results according to a plurality of reporting rules, generates a recognition report according to the modified recognition results, and stores the recognition report in the database;
   wherein the recognition results have data dependencies on each other, and when the data of the recognition results are in conflict or mutually exclusive, the integration unit modifies at least one of the recognition results in the raw result according to the reporting rules.

2. The medical image recognition system of claim 1, wherein the plurality of integrated circuits are further configured to implement:
   a digital imaging and communications in medicine (DICOM) reader, wherein the DICOM reader receives the accession number from a web server and a DICOM image file from DICOM image storage, and wherein the DICOM reader converts the DICOM image file into a portable network graphics (PNG) image in a PNG image format, and then stores the PNG image file in a PNG image storage device; wherein the DICOM image is in the DICOM format, and the PNG image file comprises the body image.

3. The medical image recognition system of claim 1, wherein an automated reporting system reads the recognition report corresponding to the accession number from the database and displays the recognition report on a display through a user interface; wherein the automated reporting system receives modified information through the user interface and writes the modified information into the database according to the accession number.

4. A medical image recognition method, comprising:
   transmitting an accession number using a first unit;
   receiving the accession number and a body image and inputting the body image into a plurality of neural network models using a recognition module; wherein each of the neural network models outputs at least one recognition result;
   returning the recognition results to the first unit using the recognition module;

storing the recognition results in a database using the first unit;
transmitting medical-record data corresponding to the accession number to the first unit using the database;
combining the accession number, the medical-record data and the recognition results into a raw result and returning the raw result to the database using the first unit;
receiving the accession number from the first unit at an integration unit implemented by the processor, reading the raw result from the database according to the accession number, modifying the raw result to recognition results according to a plurality of reporting rules, generating a recognition report according to the modified recognition results; and
storing the recognition report in the database using the integration unit;
wherein the recognition results have data dependencies on each other, and when the data of the recognition results are in conflict or mutually exclusive, the integration unit adjusts at least one of the recognition results according to the reporting rules.

5. The medical image recognition method of claim 4, comprising:
receiving the accession number from a web server and a DICOM image file from DICOM image storage by a digital imaging and communications in medicine (DICOM) reader, and converting the DICOM image file into a portable network graphics (PNG) image in a PNG image format, and then storing the PNG image into a PNG image storage device; wherein the DICOM image is in the DICOM format, and the PNG image comprises the body image.

6. The medical image recognition method of claim 4, further comprising:
reading the recognition report corresponding to the accession number from the database using an automatic reporting system and displaying the recognition report on a display through a user interface;
wherein the automatic reporting system receives a modified information through the user interface and writes the modified information into the database according to the accession number.

* * * * *